United States Patent
Hallbäck

(10) Patent No.: US 11,458,272 B2
(45) Date of Patent: Oct. 4, 2022

(54) MEDICAL PRESSURE MEASURING DEVICE AND BREATHING APPARATUS

(71) Applicant: MAQUET CRITICAL CARE AB, Solna (SE)

(72) Inventor: Magnus Hallbäck, Danderyd (SE)

(73) Assignee: MAQUET CRITICAL CARE AB, Solna (SE)

( * ) Notice: Subject to any disclaimer, the term of this patent is extended or adjusted under 35 U.S.C. 154(b) by 309 days.

(21) Appl. No.: 16/615,220

(22) PCT Filed: Jun. 21, 2017

(86) PCT No.: PCT/SE2017/050686
§ 371 (c)(1),
(2) Date: Nov. 20, 2019

(87) PCT Pub. No.: WO2018/236259
PCT Pub. Date: Dec. 27, 2018

(65) Prior Publication Data
US 2020/0155784 A1     May 21, 2020

(51) Int. Cl.
*A61M 16/08*     (2006.01)
*A61M 16/00*     (2006.01)
(Continued)

(52) U.S. Cl.
CPC .... *A61M 16/0858* (2014.02); *A61M 16/0006* (2014.02); *A61M 16/0833* (2014.02);
(Continued)

(58) Field of Classification Search
CPC .............. A61M 16/00; A61M 16/0006; A61M 16/0057; A61M 16/0096; A61M 16/022;
(Continued)

(56) References Cited

U.S. PATENT DOCUMENTS 5,813,399 A    9/1998   Isaza et al.
2003/0051553 A1   3/2003   Matsuyama et al.
(Continued)

FOREIGN PATENT DOCUMENTS

DE    102005013914 A1 *  7/2006  ......... G01L 19/0609
EP         2 233 167 A1      9/2010
(Continued)

OTHER PUBLICATIONS

English language machine translation of DE-102005013914-A1.*

*Primary Examiner* — Joseph D. Boecker
(74) *Attorney, Agent, or Firm* — Fay Kaplun & Marcin, LLP

(57) ABSTRACT

A medical device measures a pressure of a pressurized breathing gas and includes a pressure sensor arranged at a point of measurement and measures the pressure of a sample gas at a sampling point. The sampling point and the point of measurement are connected by a pressure sampling tube in which a pressure wave of the sample gas can propagate from the sampling point to the point of measurement. The tube has a sampling tube volume and an acoustic impedance. The device further includes a damping arrangement fluidly communicating with the tube. The damping arrangement includes a flow restrictor and a receptor chamber arrangement. The receptor arrangement includes a receptor chamber which receives the pressure wave. The restrictor correlates to the acoustic impedance to prevent acoustic resonance in the tube. The receptor chamber correlates at least to the tube volume to prevent acoustic resonance in the tube.

22 Claims, 3 Drawing Sheets

(51) Int. Cl.
*G01L 19/06* (2006.01)
*A61M 16/10* (2006.01)

(52) U.S. Cl.
CPC ..... *A61M 16/0866* (2014.02); *G01L 19/0609* (2013.01); *A61M 16/0096* (2013.01); *A61M 2016/0027* (2013.01); *A61M 2016/102* (2013.01)

(58) Field of Classification Search
CPC .......... A61M 16/0858; A61M 16/0866; A61M 2016/0027; A61M 2205/3331; A61M 2205/3344; G01L 19/0609
See application file for complete search history.

(56) References Cited

U.S. PATENT DOCUMENTS

| | | | |
|---|---|---|---|
| 2004/0168520 A1* | 9/2004 | Gleeson | F01D 17/08 73/756 |
| 2006/0283660 A1* | 12/2006 | Cai | F01N 1/006 181/252 |
| 2014/0190481 A1 | 7/2014 | Jam | |
| 2014/0260519 A1* | 9/2014 | Hurst | G01L 19/02 73/1.57 |
| 2015/0268120 A1* | 9/2015 | Sadig | G01L 19/0609 73/707 |

FOREIGN PATENT DOCUMENTS

| | | |
|---|---|---|
| WO | 2007/142642 A1 | 12/2007 |
| WO | 2008/070629 A2 | 6/2008 |
| WO | 2016/161036 A1 | 10/2016 |

* cited by examiner

MEDICAL PRESSURE MEASURING DEVICE AND BREATHING APPARATUS

TECHNICAL FIELD

The present disclosure relates to a medical pressure measuring device and a breathing apparatus.

BACKGROUND ART

For medical devices it is often important to measure the pressure of a fluid. This is, for example, known from measuring blood pressure. Also gaseous fluids need sometimes to be measured, such as gaseous media (i.e., gases, mixture of gases, and mixture of gases with some liquid droplets) used in breathing apparatuses. It is in this respect important that the measured pressure of the fluid is accurate. This is due to the fact that the measured pressure is used, for example, for analysing the health state of a subject and/or for controlling properties of a fluid supplied to the subject. Delivery of fluids with the wrong properties may sometimes jeopardize the safety of the subject.

For practical reasons, pressure measurements are not always possible to perform at a desired point of measurement. This can, for example, be due to the fact that a pressure measuring device requires a certain amount of space, which is not always available at the desired point of measurement. In other words, due to space constraints, it is not always practical to place a pressure measuring device at certain desired locations along a flow circuit for gaseous media. It could also be that a measurement should be performed at a point where a risk occurs that the pressure sensor could be contaminated by the exhalation gas of a subject and thus would require cleaning from time to time. Even for this reason it might be practical to not place a pressure sensor at a point for which a pressure measurement should be performed.

SUMMARY OF THE INVENTION

It has been realised that medical pressure measuring devices sometimes do not show the "right" value (i.e., the actual value) for pressure measurements although they are not malfunctioning because there may be a cause of measuring error within the design of the fluid flow system undergoing measurement. This can be the case if the pressure measurement is performed at a measurement point that is placed at a distance from a sampling point for which the pressure shall be determined and if it is assumed that the pressure at the sampling point equals the pressure at the measurement point. When measuring at a point of measurement that is at a distance from a sampling point, there is usually a pressure sampling tube arranged between the measurement point and the sampling point. It has been realised that the fact the pressure measurement device sometimes does not show the "right" value can be due to the fact that physical effects can cause the medical pressure measuring device to show a value for the fluid pressure at the measurement point that differs from the pressure of the fluid at the sampling point. It has turned out that this source of measuring error can be caused by a phenomenon called acoustic resonance, especially in connection to so-called high frequency oscillations, HFO. Since pressure waves correspond to acoustic waves, i.e. both waves relate to the fact that a gas is locally compressed and depressed, the acoustic phenomenon is present for the pressure waves as well.

The measuring error is a difference in pressure between the point of measurement where the sensor is located and the sampling point where the varying pressure is to be determined. The difference is due to the pressure wave bouncing back and forth in the tube connecting the two points. The pressure wave hits the pressure sensor with a pressure that can have very little to do with the pressure that drives the pressure wave from the sampling point.

The present disclosure relates to a medical pressure measuring device and a breathing apparatus with more reliable values (e.g., values not adversely affected by acoustic resonance) for measuring the pressure of a fluid.

The present disclosure further relates to a medical pressure measuring device and a breathing apparatus with an alternative way of measuring the pressure of a fluid.

The present disclosure also relates to a medical pressure measuring device and a breathing apparatus that compensate for distorting physical effects, such as acoustic resonance, when measuring the pressure of a fluid, or at least help to reduce the effect of these distorting physical effects.

A medical pressure measuring device, according to an exemplary embodiment of the present disclosure, measuring a pressure of a pressurized breathing gas supplied to a subject by a breathing apparatus. The medical pressure measuring device comprises a pressure sensor. The pressure sensor is arranged at a point of measurement and configured to measure the pressure of a sample gas at a sampling point. The sampling point and the point of measurement are connected by a pressure sampling tube. In the pressure sampling tube, a pressure wave of the sample gas can propagate from the sampling point to the point of measurement, and the pressure sampling tube has a sampling tube volume and an acoustic impedance.

Beside the pressure sensor, the medical pressure measuring device further comprises a damping arrangement, which is arranged to be brought into fluid communication with the pressure sampling tube. The damping arrangement comprises a flow restrictor and a receptor chamber arrangement. The receptor chamber arrangement comprises a receptor chamber. The receptor chamber arrangement is an arrangement for receiving the pressure wave of the sample gas. The flow restrictor correlates to the acoustic impedance of the pressure sampling tube, so as to prevent acoustic resonance in the pressure sampling tube. The receptor chamber correlates at least to the volume of the pressure sampling tube, so as to prevent acoustic resonance in the pressure sampling tube.

By correlating the flow restrictor and the receptor chamber as indicated, incorrect or erroneous measurement values of the pressure sensor due to acoustic resonance in a sampling tube are prevented. This allows for the pressure value to be measured at a point of measurement that corresponds more accurately to the pressure at a sampling point. In this way, a correct pressure measurement at a point distant from the sampling point is achieved.

In one embodiment of the medical pressure measuring device, the receptor chamber has a capacitance that correlates to a capacitance of the sampling tube. This is an illustrative embodiment in which acoustic resonance in the pressure sampling tube can be prevented.

In one embodiment of this disclosure, the receptor chamber has a volume that correlates to the volume of the sampling tube volume. The volume of the receptor chamber is preferably selected to be one to five times the sampling tube volume. This is an illustrative embodiment in which acoustic resonance in the pressure sampling tube can be prevented, especially in case in which the volume of the receptor chamber is basically fixed.

In one embodiment of this disclosure, the resistance of the flow restrictor substantially corresponds to the acoustic impedance of the pressure sampling tube. This is an illustrative embodiment in which acoustic resonance in the pressure sampling tube can be prevented.

In one embodiment of this disclosure, the receptor chamber arrangement comprises a resilient structure having elastic properties. The elastic properties of the resilient structure are adjusted to the volume of the pressure sampling tube. This is an illustrative embodiment in which acoustic resonance in the pressure sampling tube can be prevented, especially for non-fixed volumes of the receptor chamber. In one example, the resilient structure is a pneumatic spring, and/or an elastic membrane, and/or at least one elastic wall of the receptor chamber.

In one example, the sample gas is a pressurized breathing gas. This is an especially useful application of the inventive concept of the present disclosure because, for breathing gases, a correct pressure value is important.

In one embodiment of this disclosure, the receptor chamber arrangement comprises a pneumatic spring. This is a specific implementation of the inventive concept of the present disclosure, especially for non-fixed volumes of the receptor chamber.

In one embodiment of this disclosure, the receptor chamber comprises a resilient structure, such as an elastic membrane. This is a specific implementation of the inventive concept of the present disclosure, especially for non-fixed volumes of the receptor chamber.

In one embodiment of this disclosure, the flow restrictor comprises a porous element, for example, a microporous element. This is a specific implementation of the inventive concept of the present disclosure.

A breathing apparatus, according to an exemplary embodiment of the present disclosure, delivers pressurized breathing gas to a subject. The breathing apparatus comprises the medical pressure measuring device according to the present disclosure. The medical pressure measuring device is arranged to measure a pressure of the pressurized breathing gas.

Especially for breathing gases, a correct pressure measurement is important. Applying the inventive concept of the present disclosure to a breathing apparatus is thus an important application.

In one embodiment of this disclosure, the breathing apparatus is arranged to deliver an oscillating breathing gas pressure to the subject. The medical pressure measuring device is arranged to measure the oscillating breathing gas pressure.

In one embodiment of this disclosure, the breathing apparatus is arranged to provide high frequency oscillatory, HFO, ventilation to the subject.

In one embodiment of this disclosure, the breathing apparatus comprises a ventilator unit configured for connection to the subject via a patient circuit.

In one embodiment of this disclosure, the ventilator unit comprises a sample gas inlet for connection to the sampling tube. This allows for a design of the breathing apparatus that allows easy handling of the breathing apparatus by personnel.

In one embodiment of this disclosure, the pressure sensor is arranged within the ventilator unit. This allows for a compact design of the breathing apparatus.

In one embodiment of this disclosure, the breathing apparatus further comprises a patient circuit for connecting the ventilator unit to the subject.

In one example of this disclosure, the breathing apparatus comprises the pressure sampling tube. The pressure sampling tube is arranged between a sampling point in the patient circuit and the sample gas inlet of the ventilator unit.

In one example of this disclosure, the patient circuit comprises a Y-piece for connecting the subject to an inspiratory line and an expiratory line of the patient circuit. The sampling point is located at the Y-piece. This is a practical application of the inventive concept of the present disclosure, as the Y-piece might be a suitable point for which a pressure measurement should be performed, but where it is, at the same time, difficult to attach a pressure sensor directly at the Y-piece.

In one embodiment of this disclosure, the damping arrangement is arranged within the ventilator unit. This allows for a compact design. Further, by reducing visible components handling errors can be minimised.

In one example of this disclosure, the breathing apparatus further comprises a purge flow arrangement arranged to continuously or intermittently purge the pressure sampling tube. This has the advantage of reducing contaminants in the sampling tube, thereby reducing the risk of potentially harming the subject.

In one embodiment of this disclosure, the damping arrangement is connected, at a connection point, to the pressure sampling tube, or to a gas conducting passage connected to the sampling tube for conducting the flow of sample gas towards the point of measurement. The distance between the point of measurement and the connection point is preferably less than two meters, more preferably less than one meter, and even more preferably less than half a meter. This assures in many cases that the distance between the point of measurement and the connection point is smaller than the relevant wavelengths of the oscillations of the sample gas.

In this summary of the invention, only some of the possible embodiments and their advantages have been presented. Further embodiments and advantages will be presented in the following detailed description. Further advantages will also appear for a person skilled in the art when reading the detailed description and/or when applying/implementing the present disclosure.

BRIEF DESCRIPTION OF THE DRAWINGS

In the following figures.

In the figures, the same reference numerals refer to the same elements throughout the figures.

DETAILED DESCRIPTION

Figure 1:
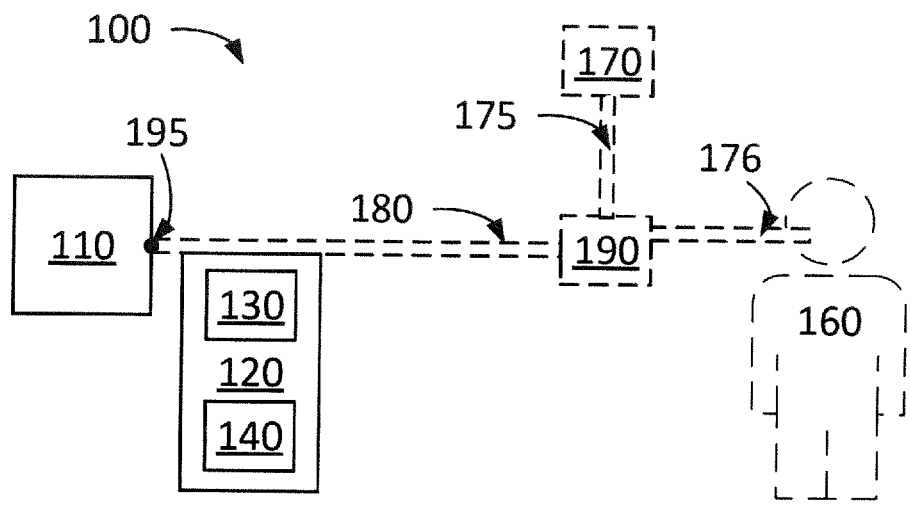
FIG. 1 depicts schematically an embodiment of a medical pressure measuring device according to the present disclosure.

FIG. 1 depicts schematically an embodiment of a medical pressure measuring device 100. In the following, the medical pressure measuring device 100 will be denoted device 100. The device 100 comprises a pressure sensor 110 and a damping arrangement 120.

The device 100 is suitable for measuring a pressure of a pressurized breathing gas supplied to a subject 160 by a breathing apparatus. Embodiments of the breathing apparatus will be described later, for example in relation to FIG. 3. The subject 160 can be a human being. The subject 160 can be an animal. Examples of breathing gases are air, oxygen, an oxygen-nitrogen mixture, a helium-oxygen mixture, so called "Heliox", or any other gas comprising one or several of the aforementioned components. In one example the device 100 is arranged for measuring a pressure of a pressurized breathing gas supplied to the subject 160.

The pressure sensor 110 is arranged at a point of measurement 195. The pressure sensor 110 can be any prior art pressure sensor. The pressure sensor 110 is configured to measure the pressure of a sample gas at a sampling point 190. The sampling point 190 is placed at a distance from the point of measurement 195. The sample gas is thus, in general, present at the point of measurement 195 and at the sampling point 190. The sample gas can be a pressurized breathing gas. It is sufficient that the pressure wave of the sample gas can propagate from the sampling point 190 to the point of measurement 195. In one example, the sampling point 190 is located in an apparatus for supplying a supply gas to the subject 160. The apparatus for supplying a supply gas can comprise a supply gas storage 170. The apparatus for supplying a supply gas can comprise a first gas passage 175 and/or a second gas passage 176. The first and/or second gas passage(s) 175, 176 can be arranged to transport the supply gas from the gas storage 170. The first and/or second gas passage(s) 175, 176 can be arranged to transport the supply gas to the subject 160. The sampling point 190 can be arranged at the first and/or second gas passage(s) 175, 176. The supply gas can be the breathing gas.

The sampling point 190 and the point of measurement 195 are connected by a pressure sampling tube 180. The pressure sampling tube 180 can consist of any suitable material. The pressure sampling tube 180 is arranged so that a pressure wave of the sample gas can propagate through it from the sampling point 190 to the point of measurement 195. The pressure sampling tube 180 has a sampling tube volume $V_0$. The pressure sampling tube has an acoustic impedance $Z_0$. The acoustic impedance for the pressure sampling tube 180 can, in one example be defined as $$Z_0 = \sqrt{\frac{L_0}{C_0}},$$

wherein the acoustic impedance can be expressed in [mbar/(mL/s)]. $L_0$ denotes the inductance of the gas in the sampling tube, and can, in one example, be expressed as $L_0 = \rho \cdot l_0 / A_0$, where $\rho$ denotes the density of the sampling gas, $l_0$ denotes the length of the sampling tube, and $A_0$ denotes the cross sectional area of the sampling tube. In this example, it has been assumed that the tube has a basically constant cross section. It should, however, be emphasised that the tube can have any form or shape profile for the cross sectional area. The above formula can then be adapted to a varying cross-sectional profile or the like. $C_0$ denotes the capacitance of the pressure sampling tube 180. In one example, the capacitance of the sampling tube is defined as $C_0 = l_0 \cdot A_0 / (\kappa \cdot P_{bar})$, wherein $\kappa$ denotes the ratio between the specific heat at constant pressure and constant volume, and wherein $P_{bar}$ is the absolute pressure of the sampling gas. The pressure sampling tube 180 is, in one example, not incorporated in the pressure measuring device 100. In one example, the sampling tube is incorporated in the pressure measuring device 100. The formula $$Z_0 = \sqrt{\frac{L_0}{C_0}}$$

is, in one example, used for a lossless pressure sampling tube 180. This formula can be adapted for a non-lossless sampling tube 180. Alternatively, or additionally, the value $Z_0$ can be measured for any given sampling tube 180. Then, no specific formula is needed for $Z_0$.

The damping arrangement 120 is arranged to be brought in fluid communication with the pressure sampling tube 180. In one example, the damping arrangement 120 is directly connected to the pressure sampling tube 180. In one example, at least one intermediate element is arranged between the damping arrangement 120 and the pressure sampling tube 180.

The damping arrangement 120 comprises a flow restrictor 130. The flow restrictor 130 correlates to the acoustic impedance of the pressure sampling tube 180. In one example, the flow restrictor 130 correlates to the acoustic impedance of the pressure sampling tube 180 so as to prevent acoustic resonance in the pressure sampling tube 180. Here, and in the whole document, the term "correlates" relates to the fact that one or more physical quantities of objects, such as one or more physical quantities of the flow restrictor 130 and/or the sampling tube 180, relate to each other in such a way, that a specific purpose is achieved by their relation, such as preventing acoustic resonance in the pressure sampling tube 180. Specific examples will follow. The term "correlates" can relate to adjustment(s) and/or matching(s) of these one or more quantities for achieving the specific purpose.

Here, and in the whole document, the term "adjusted" or "adjustment" of any quantity/quantities can relate to the fact that the adjustment is performed so as to prevent acoustic resonance in the pressure sampling tube 180 from affecting pressure measurements made by the pressure sensor 110. In one example, the correlation of the flow restrictor 130 to the acoustic impedance of the pressure sampling tube 180 so as to prevent acoustic resonance in the pressure sampling tube 180, is an adjustment of the flow restrictor 130 to the acoustic impedance of the pressure sampling tube 180 and comprises that the resistance of the flow restrictor 130 is adjusted to the acoustic impedance of the pressure sampling tube 180. In one example, the adjustment comprises that the resistance R of the flow resistor 130 matches the acoustic impedance $Z_0$ of the pressure sampling tube 180. In one example, the matching comprises that the resistance R of the flow resistor 130 is adapted to the acoustic impedance $Z_0$ of the pressure sampling tube 180. The adaption can comprise that the resistance R of the flow resistor 130 equals the acoustic impedance $Z_0$ of the pressure sampling tube 180, or does not deviate more than 50% from the acoustic impedance $Z_0$, preferably not more than 35% from the acoustic impedance $Z_0$, and even more preferably not more than 20% from the acoustic impedance $Z_0$. The adaption can comprise that the ratio $R/Z_0$ is between 0.5 and 2. The adaption can comprise that the ratio $R/Z_0$ is between 0.316 and 3.16. The adaption can comprise that the ratio $R/Z_0$ is between 0.1 and 10.

The damping arrangement 120 comprises a receptor chamber arrangement 140 for receiving the pressure wave of the sample gas. The receptor chamber arrangement 140 comprises a receptor chamber 141. The receptor chamber arrangement 140 is, in one example, arranged for receiving the pressure wave of the sample gas. The receptor chamber 141 is in one example arranged for receiving the pressure wave of the sample gas. The receptor chamber 141 has an internal volume $V_C$. In one example, the internal volume $V_C$ is a fixed volume. In one example, the internal volume $V_C$ is variable. This is further described in relation to FIG. 2. The receptor chamber 141 is preferably in fluidic connection with the pressure sampling tube 180. The receptor chamber 141 correlates at least to the volume $V_0$ of the pressure sampling tube 180, so as to prevent acoustic resonance in the pressure sampling tube. In one example the capacitance $C_C$ of the receptor chamber 141 is adjusted to the capacitance $C_0$ of the pressure sampling tube 180. In one example, the capacitance adaptation comprises that the capacitance $C_C$ of the receptor chamber 141 and the capacitance $C_0$ of the pressure sampling tube 180 are of the same order of magnitude.

In one example, the capacitance of the receptor chamber 141 can be written as $C_C = k \cdot V_0/P_{bar}$, where k is a constant. In one example, the adapting of capacitance comprises designing the receptor chamber so that its capacitance $C_C$ equals a value of $k \cdot V_0/P_{bar}$, wherein k is a value between 1 and 5. In one example, k is a value between 1.5 and 2.5. In one example, k is approximately 2. Simulations have shown that the aforementioned ranges of k provide reasonable results for a specific setup of a breathing apparatus which is described in relation to FIG. 3. The aforementioned relationships regarding the capacitance $C_C$ are especially useful for fixed volumes $V_C$. In one example, the volume of the receptor chamber 141 is preferably one to five times the volume of the sampling tube 180. For a fixed volume of the receptor chamber 141, these values have turned out to provide the right amount of gas in the receptor chamber 141 for the gas to be compressed and/or decompressed by the pressure waves of the sampling gas propagating into the receptor chamber 141, without causing any significant reflection of the pressure waves. Tests have revealed that lower volumes $V_C$ (i.e, $V_C < V_0$) in general do not provide enough gas to compress/decompress so that the acoustic resonance in the pressure sampling tube 180 will not be prevented. Test have also revealed that higher volumes $V_C$ (i.e., $V_C > 5V_0$) in general provide too much damping, so that the pressure signal in the pressure sensor 110 might no longer correspond to the pressure at the sampling point 190. However, it should be noted that these borders are not distinct and that the difference between the pressure measured at the measurement point and the pressure at the sampling point increases gradually.

As an example, a pressure sampling tube with a length of 1.8 m would have a resonance frequency of 47 Hz for a quarter wavelength in air at a normal temperature of 21° C. Acoustic resonance can prevent the pressure sensor 110 from measuring at the point of measurement 195 the same value as would be measured at the sampling point 190 since the pressure at the point of measurement can be affected by standing waves arising in the pressure sampling tube 180. By arranging the damping arrangement, especially by adjusting the flow restrictor 130 to the acoustic impedance of the pressure sampling tube 180 and by adjusting the receptor chamber 141 to at least the volume of the pressure sampling tube 180, this acoustic resonance can be prevented. Thereby, the pressure measurement at the point of measurement 195 will correspond to the pressure at the sampling point 190. The pressure sensor 110 can thus provide a correct value for a pressure measurement at the sampling point 190, although the sampling point 190 and the point of measurement 195 are placed at a distance from each other. The medical pressure measuring device 100 as described in relation to FIG. 1 is thus designed to prevent acoustic resonance in the pressure sampling tube. Stated in other words, the acoustic resonance is prevented by allowing a pressure wave of the sampling gas to "continue" into the damping arrangement 120 without being reflected in such a way that the reflected pressure wave significantly affects the result of a pressure measurement obtained at the point of measurement. It should be understood that in practice no complete extinction of any reflection can be achieved. However, in the context of this application, the term "prevent" should be interpreted in such a way that the effect of any remaining reflection is so low that it will not significantly affect a pressure measurement. As an example, a remaining reflection will not affect significantly a pressure measurement if the effect of the remaining reflection on the measured pressure value is lower than the measurement uncertainty of the pressure sensor. In other words, the damping arrangement 120 is, in this example, able to attenuate the effect of acoustic impedance on the measured pressure at the measuring point to the degree that it is less than the measuring error of the pressure sensor 110, which means that acoustic impedance has negligible effect, or no substantial effect, on the measured pressure.

Figure 2:
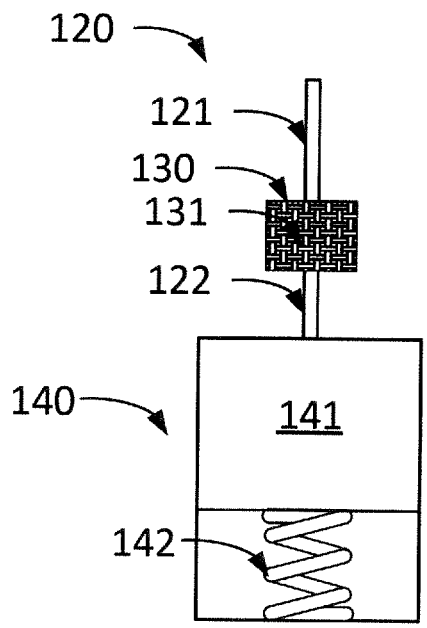
FIG. 2 depicts schematically an embodiment of a damping arrangement according to the present disclosure.

FIG. 2 depicts schematically an embodiment of a damping arrangement 120 according to the present disclosure in greater detail. The damping arrangement 120 comprises the flow restrictor 130 and the receptor chamber arrangement 140. In the shown example, the damping arrangement 120 further comprises a first damping arrangement passage 121 and a second damping arrangement passage 122. In the remainder of the description of FIG. 2, these passages will only be denoted for brevity's sake as first passage 121 and second passage 122. The first passage 121 can be situated between the flow restrictor 130 and the pressure sampling tube 180. For example, the damping arrangement 120 may be arranged to be brought into fluid communication with the pressure sampling tube 180 via an inlet of the damping arrangement. This inlet may constitute an inlet of the first damper arrangement passage 121 and, thus, serve to convey the pressure wave propagating through the pressure sampling tube towards the flow restrictor 130 and the receptor arrangement 140 of the damping arrangement. The second passage 122 can be situated between the receptor chamber arrangement 140 and the flow restrictor 130. The first and/or second passage 121, 122 can be useful for allowing an easier design of the damping arrangement 120 and/or adaptation of the damping arrangement 120 to the pressure sampling tube 180 or any other element. Preferably, the length of the first and/or second passage 121, 122 is short in comparison to the length of the pressure sampling tube 180. Preferably, the physical properties of the first and/or second passage 121, 122 are negligible in comparison to the physical properties of the flow restrictor 130 and/or the receptor chamber arrangement 140. This applies especially to the volume of the first and/or second passage 121, 122, and/or to their capacitance and/or resistance. In case the physical properties are not negligible, the corresponding properties of the flow restrictor 130 and/or the receptor chamber arrangement 140 have to take into account the properties of the first and/or second passage 121, 122.

In one example of this disclosure, the flow restrictor 130 comprises a porous element 131. The porous element 131 can be a microporous element. By using a porous element 131, the flow of the sampling gas can be effectively restricted. Especially, it can be prevented that pressure wave reflections are transmitted back from the damping arrangement 120 into the pressure sampling tube 180 and/or other elements. A porous element 131 also allows easy adaption of the resistance R of the flow restrictor 130.

In one example, the flow restrictor 130 comprises a narrow tube section. By using a narrow tube section, the flow of the sampling gas can be effectively restricted. Especially, it can be prevented that pressure wave reflections are transmitted back from the damping arrangement 120 into the pressure sampling tube 180 and/or other elements.

The internal volume $V_C$ of the receptor chamber 141 of the receptor chamber arrangement 140 can be fixed as described in relation to FIG. 1. The internal volume $V_C$ can also instead be flexible. In case the internal volume $V_C$ is flexible, the elastic properties of the receptor chamber arrangement 140 can be taken into account. The receptor chamber arrangement 140 can comprise a resilient structure having elastic properties. This can, for example, be a spring 142, and/or a metal bellow, and/or an elastic membrane, and/or at least one elastic wall of the receptor chamber 141. The elastic properties of the receptor chamber arrangement 140 can comprise the elastic properties of the receptor chamber 141. In one example, the elastic properties comprise the elastic properties of at least one outer wall of the receptor chamber 141. As an example, the receptor chamber 141 can comprise at least one elastic wall. As an example, the receptor chamber 141 can comprise a resilient structure, such as an elastic membrane. In one example, the receptor chamber arrangement 140 comprises a spring 142. At least one wall of the receptor chamber 141 can be attached to the spring 142. Thus, the walls of the inner chamber 141 can be rigid but still behave as a resilient structure and/or provide a flexible inner volume for the receptor chamber 140. The spring 142 is only drawn schematically. It should be understood that certain spring arrangements might require additional elements. These additional elements are not shown in FIG. 2; however, it is known in the art how to implement springs in medical devices. By adjusting the properties of the spring 142 and/or another resilient structure, it is possible to gain additional degrees of freedoms for adjusting the receptor chamber 141 at least to the volume $V_0$ of the pressure sampling tube 180. Especially, it facilitates adjusting the capacitance $C_C$ of the receptor chamber 141 to the capacitance $C_0$ of the pressure sampling tube 180.

Figure 3:
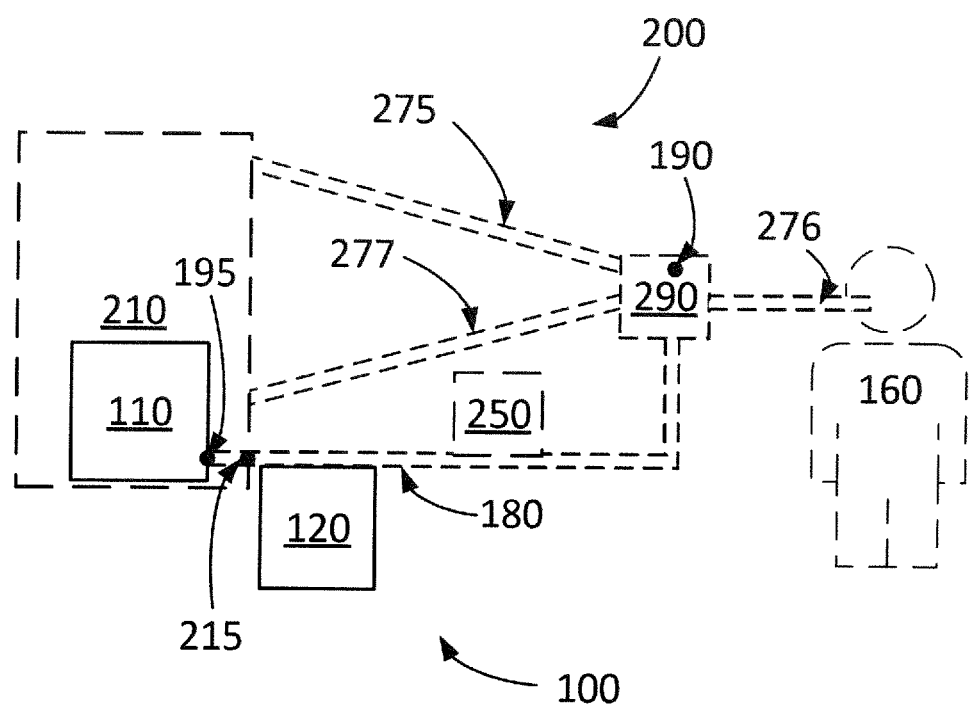
FIG. 3 depicts schematically an embodiment of a breathing apparatus according to the present disclosure.

FIG. 3 depicts schematically an embodiment of a breathing apparatus 200 according to the present disclosure. The breathing apparatus 200 is a breathing apparatus for delivery of pressurized breathing gas to a subject 160. Elements that have been described in relation to FIG. 1 and FIG. 2 are not described here again. These elements, which are indicated by the same reference number, have the same functioning and attributes unless described differently. The breathing apparatus 200 comprises the medical pressure measuring device 100. The medical pressure measuring device 100 is arranged to measure a pressure of the pressurized breathing gas. Examples of the breathing gas have been described in relation to FIG. 1. Examples of breathing apparatuses for delivery of pressurized breathing gas to a subject are well known in the art. A breathing apparatus according to the present disclosure comprises, in addition to known breathing apparatus, also the medical pressure measuring device as described in relation to FIG. 1 and/or 2, especially the damping arrangement 120.

The breathing apparatus 200 can be arranged to deliver an oscillating breathing gas pressure to the subject 160. For example, the breathing apparatus can be arranged to deliver so-called high frequency oscillatory ventilation, HFO-ventilation, to the subject 160. A breathing apparatus arranged to deliver HFO-ventilation to a subject is disclosed in WO2014/046583. The medical pressure measuring device 100 may advantageously be arranged to measure the oscillating breathing gas pressure.

The breathing apparatus can comprise a ventilator unit 210. In one example, the point of measurement 195 is inside the ventilator unit 210. The breathing apparatus can have a patient circuit for connecting the ventilator unit 210 to the subject 160 so the ventilator unit 210 supplies pressurized breathing gas to the subject 160. The ventilator unit 210 can be arranged for connection to the subject 160 via the patient circuit. The patient circuit can have any design. A schematic embodiment of a patient circuit is depicted in FIG. 3. In this embodiment, the patient circuit can comprise a first, second, and third breathing apparatus passage 275, 276, 277, which in the following will be denoted only first, second, and third passage 275, 276, 277, respectively, for the sake of brevity. The patient circuit can further comprise a so-called Y-piece 290.

The first passage 275 can be arranged in fluid connection between the ventilator unit 210 and the Y-piece 275. The second passage 276 can be in fluid connection between the Y-piece 290 and the subject 160. The third passage 277 can be in fluid connection between the Y-piece 290 and the ventilator unit 210. In one example, the first passage 275 is part of an inspiratory line of the patient circuit. In one example, the third passage 277 is part of an expiratory line of the patient circuit. In one example, the second passage 276 is part of a patient connection for connecting the subject 160 to the inspiratory line and expiratory line, respectively.

In one example, the sampling point 190 is located at the Y-piece 290. The pressure sampling tube 180 can be arranged between the Y-piece 290 and the ventilator unit 210. The ventilator unit 210 can comprise a sample gas inlet 215. The pressure sampling tube 180 can be arranged between the Y-piece 290 and the sample gas inlet 215 of the ventilator unit 210. The pressure sensor 110 can be arranged inside the ventilator unit 210. The pressure sampling tube 180 can be part of the breathing apparatus 200. The damping arrangement 120 can be arranged outside the ventilator unit 210. Alternatively, the damping arrangement 120 can be arranged inside the ventilator unit 210 (not shown in the figure).

The medical pressure measuring device 100 and/or the breathing apparatus 200 can have a control unit (not shown). The control unit can be part of the ventilator unit 210. The control unit can be part of the pressure sensor 110 and/or connected to it. The control unit can be connected to at least one sensor, such as a temperature sensor, a pressure sensor for measuring the pressure of the ambient air, a sensor for determining the composition of the sampling gas, or the like. The control unit can be adapted to correct the measured pressure of the sample gas based on at least one quantity, comprising any of the temperature of the sample gas, the temperature of the ambient air, the composition of the sample gas, and the pressure of the ambient air. This at least one quantity might have some effect on the measurement of the sample gas. Whereas the effect of the acoustic resonance is treated by the damping arrangement 120, the possible effect of the at least one quantity is usually less complex and can, in general, be compensated for by software functions, e.g., by software functions executed by the control unit.

In one example, the breathing apparatus comprises a purge flow arrangement 250. The purge flow arrangement 250 can be arranged to continuously or intermittently purge the pressure sampling tube 180.

Figure 4A:
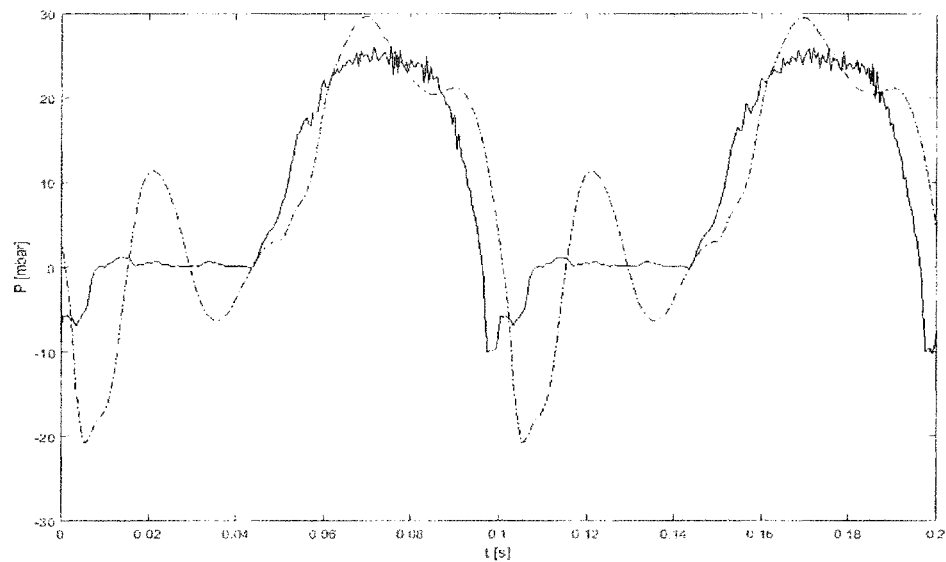
FIGS. 4a and 4b depict comparisons between pressure measurements of a pressure measuring device according to the present disclosure and a prior art pressure measuring device.
Figure 4B:
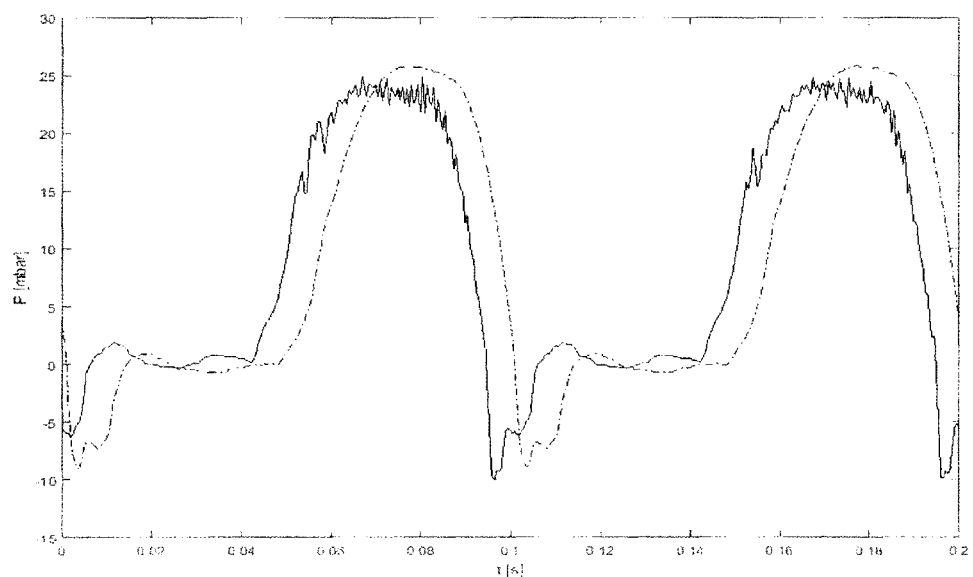

FIGS. 4a and 4b depict comparisons between pressure measurements of a pressure measuring device according to the present disclosure and a prior art pressure measuring device. In FIGS. 4a and 4b, a sampling tube with a length of 1.8 m and an inner diameter of 3 mm was used. The pressure sampling tube has an acoustic impedance $Z_0$ of 584 mbar/(L/s) and a sampling tube volume $V_0$ of 12.7 mL. A first pressure sensor $P_Y$ was placed at a Y-piece, one end of the sampling tube was attached to the Y-piece, and a second pressure sensor $P_S$ was placed at the end of the sampling tube which was not attached to the Y-piece. A test lung with an internal volume of 250 mL was connected to the Y-piece via a small gas conducting passage. The damping arrangement comprised a filter acting as flow restrictor and a receptor chamber with a variable internal volume $V_C$. The variable internal volume $V_C$ could vary between 0 and 40 mL. The resistance R of the flow resistor was 525 mbar/(L/s) at $\Delta p$=21 mbar and 700 mbar/(L/s) at $\Delta p$=46 mbar, wherein $\Delta p$ denotes the pressure drop over the filter. Pressurized gas was delivered to the test lung at a pressure that varied in accordance with a partly truncated sine curve with a frequency of 10 Hz, so as to cause pressure waves oscillating at the sine frequency and at least some of its overtones to propagate through the sampling tube.

For this testing setup, an inner volume $V_C$ of 0 corresponds to a de-activated damping arrangement. Measurement results revealed that an increased inner volume $V_C$, starting at 0, leads to a more accurate pressure measurement at the second pressure sensor $P_S$ when compared to the first sensor $P_Y$. Above $V_C$=40 mL the accuracy of the pressure measurement started decreasing again due to the fact that such a comparably high volume has a dampening effect on the pressure signal.

In FIGS. 4a and 4b, the vertical axis depicts the measured pressure in mbar, and the horizontal axis depicts the time in seconds. The continuous line depicts the measurement signal of $P_Y$, i.e., at the sampling point. The dash-dotted line depicts the measurement signal of $P_S$, i.e., at the point of measurement.

FIG. 4a depicts the situation when the damping arrangement was de-activated, i.e. $V_C$=0. This corresponds to the situation where the inventive damping arrangement of the present disclosure is not applied. As can be seen from FIG. 4a, the pressure signals differ substantially. As an example, between 0.11 s and 0.14 s the measurement of $P_Y$ is basically constant, whereas the measurement of $P_S$ oscillates considerably. In such a setup, the values of the pressure signals differ and a measurement at the point of measurement differs substantially from a measurement at the sampling point.

FIG. 4b depicts the situation when an internal volume of $V_C$=20 mL was applied. This corresponds to employment of a damping arrangement according to the inventive concept of the present disclosure. As can be seen, the two measurement curves correspond quite well to each other when compensating for a small time-shift between them. The time-shift between the two measurement curves is at least partly due to the fact that the pressure sensors are placed at different points and that the speed of sound causes a time-delay for a signal from the first pressure sensor before it reaches the second pressure sensor. In sum, because both of the curves have substantially the same form despite the time shift, this means that the pressure measurement at the point of measurement corresponds substantially to the pressure measurement at the sampling point because the effect of acoustic impedance and/or of other sources of error have been negated by the damping arrangement.

In one embodiment of the present disclosure, a compensation for the time-delay is implemented. This can be performed by any arrangements known in the art. In practice, however, such a compensation might in many cases not be needed as a time delay of a few milliseconds is irrelevant for the purpose of pressure measurements. In many cases, the maximum and/or minimum value of the pressure might be of far more importance.

The inventive concept of the present disclosure has been described in relation to different embodiments and some of the advantages have been shown based on presented measurement results. It should be understood that different embodiments disclosed herein can be combined and that features described in relation to an embodiment which were discussed in one figure easily can be applied to embodiments discussed in relation to other figures. Further, the advantages of the inventive concept of the present disclosure have been shown for one specific example. Measurements and simulation have shown that by applying the inventive concept of the present disclosure to other setups with possibly largely deviating values for quantities as those described in relation to FIGS. 4a and 4b, may still achieve corresponding advantages for these other setups as well.

List of Elements

100 Medical pressure measuring device
110 Pressure sensor
120 Damping arrangement
121 First (damping arrangement) passage
122 Second (damping arrangement) passage
130 Flow restrictor
131 Porous element
140 Receptor chamber arrangement
141 Receptor chamber
142 Spring
160 Subject
170 Gas storage
175 First passage
176 Second passage
180 Pressure sampling tube
190 Sampling point
195 Point of measurement
200 Breathing apparatus
210 Ventilator unit
215 Sample gas inlet
250 Purge flow arrangement
275 First (breathing apparatus) passage
276 Second (breathing apparatus) passage
277 Third (breathing apparatus) passage
290 Y-piece

The invention claimed is:

1. A medical pressure measuring device for measuring a pressure of a pressurized breathing gas supplied to a subject by a breathing apparatus, comprising:
a pressure sensor arranged at a point of measurement, wherein the pressure sensor is configured to measure the pressure of a sample gas at a sampling point, wherein the sampling point and the point of measurement are connected by a pressure sampling tube so that a pressure wave of the sample gas is able to propagate from the sampling point to the point of measurement, and wherein the pressure sampling tube has a sampling tube volume and an acoustic impedance; and a damping arrangement arranged to be brought into fluid communication with the pressure sampling tube, wherein the damping arrangement comprises a flow restrictor and an associated receptor chamber arrangement, wherein the receptor chamber arrangement comprises a receptor chamber receiving the pressure wave of the sample gas, the flow restrictor correlating to the acoustic impedance of the pressure sampling tube and the receptor chamber correlating at least to the volume of the pressure sampling tube so as to prevent acoustic resonance in the pressure sampling tube from affecting pressure measurements made by the pressure sensor.

2. The medical pressure measuring device of claim 1, wherein the receptor chamber has a capacitance that correlates to a capacitance of the sampling tube.

3. The medical pressure measuring device of claim 1, wherein the receptor chamber has a volume that correlates to the volume of the sampling tube volume.

4. The medical pressure measuring device of claim 1, wherein the receptor chamber volume is selected to be one to five times the sampling tube volume.

5. The medical pressure measuring device of claim 1, wherein the resistance of the flow restrictor is adapted to the acoustic impedance of the pressure sampling tube.

6. The medical pressure measuring device of claim 1, wherein the receptor chamber arrangement comprises a resilient structure including one of a pneumatic spring, an elastic membrane, and at least one elastic wall of the receptor chamber, having elastic properties and wherein the elastic properties of the resilient structure is adjusted to the volume of the pressure sampling tube.

7. The medical pressure measuring device of claim 1, wherein the sample gas is a pressurized breathing gas.

8. The medical pressure measuring device of claim 1, wherein the effect of acoustic resonance in the pressure sampling tube is attenuated by the damping arrangement so that acoustic resonance effect on pressure measurement by the pressure sensor is less than measurement error intrinsic to the pressure sensor.

9. The medical pressure measuring device of claim 1, wherein the flow restrictor comprises a porous element.

10. The medical pressure measuring device of claim 1, wherein the flow restrictor comprises a microporous element.

11. A breathing apparatus for delivery of pressurized breathing gas to a subject, comprising:

a medical pressure measuring device, including:
  i. a pressure sensor arranged at a point of measurement, wherein the pressure sensor is configured to measure the pressure of a sample gas at a sampling point, wherein the sampling point and the point of measurement are connected by a pressure sampling tube so that a pressure wave of the sample gas is able to propagate from the sampling point to the point of measurement, and wherein the pressure sampling tube has a sampling tube volume and an acoustic impedance; and
  ii. a damping arrangement arranged to be brought into fluid communication with the pressure sampling tube, wherein the damping arrangement comprises a flow restrictor and an associated receptor chamber arrangement, wherein the receptor chamber arrangement comprises a receptor chamber receiving the pressure wave of the sample gas, the flow restrictor correlating to the acoustic impedance of the pressure sampling tube and the receptor chamber correlating at least to the volume of the pressure sampling tube so as to prevent acoustic resonance in the pressure sampling tube from affecting pressure measurements made by the pressure sensor, wherein the medical pressure measuring device is arranged to measure a pressure of the pressurized breathing gas.

12. The breathing apparatus of claim 11, wherein the breathing apparatus is arranged to deliver an oscillating breathing gas pressure to the subject and wherein the medical pressure measuring device is arranged to measure the oscillating breathing gas pressure.

13. The breathing apparatus of claim 11, wherein the breathing apparatus is arranged to provide high frequency oscillatory ("HFO") ventilation to the subject.

14. The breathing apparatus of claim 11, further comprising:

a ventilator unit configured for connection to the subject via a patient circuit.

15. The breathing apparatus of claim 14, wherein the ventilator unit comprising a sample gas inlet which is configured to connect to the sampling tube.

16. The breathing apparatus of claim 14, wherein the pressure sensor is arranged within the ventilator unit.

17. The breathing apparatus of claim 14, further comprising:

the patient circuit connecting the ventilator unit to the subject.

18. The breathing apparatus of claim 17, further comprising:

the pressure sampling tube arranged between the sampling point in the patient circuit and the sample gas inlet of the ventilator unit.

19. The breathing apparatus of claim 17, wherein the patient circuit includes a Y-piece configured to connect the subject to an inspiratory line and an expiratory line of the patient circuit, the sampling point being located at the Y-piece.

20. The breathing apparatus of claim 14, wherein the damping arrangement is arranged within the ventilator unit.

21. The breathing apparatus of claim 11, wherein the pressure sampling tube is configured to be continuously or intermittently purged.

22. The breathing apparatus of claim 11, wherein the effect of acoustic resonance in the pressure sampling tube is attenuated by the damping arrangement so that an acoustic resonance effect on pressure measurement by the pressure sensor is less than measurement error intrinsic to the pressure sensor.

* * * * *